United States Patent [19]

Kay et al.

[11] Patent Number: 4,874,806
[45] Date of Patent: Oct. 17, 1989

[54] EMULSION PAINT

[75] Inventors: Peter D. Kay, Hartlepool; Keith McDonald, Middlesbrough, both of England

[73] Assignee: Tioxide Group PLC, London, England

[21] Appl. No.: 218,216

[22] Filed: Jul. 13, 1988

[30] Foreign Application Priority Data

Jul. 25, 1987 [GB] United Kingdom ............... 8717667

[51] Int. Cl.$^4$ ................ C08K 5/16; C08L 31/04; C08L 31/02; C07F 7/28
[52] U.S. Cl. ................ 524/204; 524/247; 524/249; 524/524; 524/563
[58] Field of Search ............ 524/204, 247, 249, 524, 524/563

[56] References Cited

U.S. PATENT DOCUMENTS

| | | |
|---|---|---|
| 3,694,475 | 9/1972 | Brook et al. |
| 3,892,791 | 7/1975 | Brook et al. ................ 524/243 |
| 4,022,742 | 5/1977 | Yoshimura et al. |
| 4,544,760 | 10/1985 | Keogh ................ 428/389 |
| 4,550,055 | 10/1985 | Lavallee ................ 428/389 |
| 4,621,148 | 11/1986 | Barfurth et al. ................ 528/17 |
| 4,670,523 | 6/1987 | Lavallee ................ 524/204 |

FOREIGN PATENT DOCUMENTS

| | | |
|---|---|---|
| 51-033890 | 9/1976 | Japan . |
| 53-098393 | 8/1978 | Japan . |
| 0096056 | 6/1982 | Japan ................ 524/204 |
| 922456 | 4/1963 | United Kingdom . |
| 977145 | 12/1964 | United Kingdom . |
| 1362054 | 7/1974 | United Kingdom . |
| 1485343 | 9/1977 | United Kingdom . |

Primary Examiner—Herbert J. Lilling
Attorney, Agent, or Firm—Banner, Birch, McKie & Beckett

[57] ABSTRACT

An emulsion paint of an improved shear resistance has been developed containing as a filling agent a titanium chelate which is the reaction product of a titanium orthoester, a glycol a glycol ether, an alkanolamine and an alpha-hydroxy carboxylic acid.

17 Claims, No Drawings

EMULSION PAINT

This invention relates to emulsion paints containing titanium chelates and to methods for their manufacture.

According to the invention an emulsion paint comprises an aqueous dispersion of a film-forming polymer and a titanium chelate comprising the reaction product of a titanium orthoester, a glycol or glycol ether, an alkanolamine and an alpha-hydroxy carboxylic acid.

Preferably also the titanium chelate also is a reaction product of a base.

Also according to the present invention a method for the manufacture of an emulsion paint comprises mixing under shear an aqueous dispersion of a film-forming polymer with a titanium chelate as hereinbefore described and any other necessary emulsifying and stabilising agents, and transferring the so-prepared mixed emulsion paint into a container.

The paints of the present invention exhibit a slower rate of gel formation than those including titanium chelates presently in use in industry but the strength of the gel formed after a week or more is similar to or greater than that of paints containing those chelates presently in use. This slower rate of gel formation leads to a number of advantages in the production of thixotropic emulsion paints. For instance, it is possible to fill more containers during the packing operation before the paint becomes too viscous to flow. Also, the titanium chelates used are easier to incorporate into the emulsion paint since they have a lesser tendency to form areas of localised gellation in the paint. Further, there is less likelihood of a layer of gelled paint forming on the sides of the mixing vessel. Most importantly, however, the paints of this invention exhibit an improvement in what has been termed herein "shear-resistance". It is well known that, with the titanium chelates currently used to gel emulsion paints, a lower gel strength is generally observed for paint made on an industrial plant than on a similar paint made in a laboratory. Some of the potential gelling ability is lost due to the shearing forces to which the paint is subjected. The products of this invention are less prone to loss of potential gel strength due to this mechanism. This enables a paint manufacturer to produce an emulsion paint with less variation in structure from batch to batch than with currently available titanium gelling agents.

The titanium chelates present in the paints of the present invention are reaction products of a titanium orthoester and one or more of the other named reactants. Any orthoester can be used but usually those having the general formula $Ti(OR)_4$ in which R represents an alkyl group containing from 2 to 10 carbon atoms, preferably 2 to 4 carbon atoms will be employed. In the general formula quoted the R groups can be the same or different. Typical examples of titanium orthoesters having this general formula are titanium tetraisopropoxide, titanium tetrabutoxide and titanium tetrahexoxide.

Glycols which can be used contain two free hydroxy groups but the glycol ethers which can be used contain one or more free hydroxy groups. Typical glycols are the alkylene glycols such as ethylene glycol, 1,2-propanediol (propylene glycol), 1,3-propanediol, 1,2-butylene glycol and 2-methyl-2,4-pentanediol (hexylene glycol). Preferably alkylene glycols in which each alkylene group contains not more than 6 carbon atoms are used.

Examples of glycol ethers are the mono alkyl ethers of an alkylene glycol containing up to 6 carbon atoms in the alkylene group such as of ethylene glycol, of diethylene glycol or of triethylene glycol where the alkyl group contains 1 to 4 carbon atoms, such as 2-methoxy ethanol, 2-ethoxy ethanol, 2-isopropoxy ethanol and 2-n-butoxy ethanol.

Mixtures of glycols and/or different glycol ethers can be used.

Any alkanolamine can be used to manufacture the titanium chelates used in paints of the present invention and the alkanolamine can be a monoalkanolamine, a dialkanolamine or a trialkanolamine as desired. Typical alkanolamines are monoethanolamine, diethanolamine, triethanolamine, diisopropanolamine and triisopropanolamine. If desired mixtures of two or more different alkanolamines can be used.

Any alpha-hydroxy acid can be used to prepare the chelates used in paints of the present invention and typical acids are the hydroxy mono-carboxylic acids and the hydroxy di-carboxylic acids and can contain one or more hydroxy groups in the molecule provided at least one is in the alpha position. Typical examples of acids are lactic acid or glycolic acid. Mixtures of two different alpha hydroxy acids can be used if desired.

The most preferred chelates used in paints of the present invention are those which are reacted, in addition, with a base. The base can be either inorganic or organic and typical inorganic bases are the alkali metal hydroxides, carbonates or bicarbonates or ammonia or ammonium hydroxide. Particularly useful are the sodium and potassium hydroxides, carbonates and bicarbonates.

Although usually an inorganic base can be reacted with the chelate it is possible to use an organic base which itself can be an alkanolamine. In such a case it is possible to use any of the previously mentioned alkanolamines or mixed alkyl alkanolamine such as aminomethyl propanol.

The chelates to be used in paints of the present invention are usually prepared by reacting the chosen titanium orthoester with the chosen other ingredients in the presence or absence of a solvent as is appropriate.

For a chelate which is the reaction product of the orthoester, glycol or glycol ether, alkanolamine and alpha-hydroxy carboxylic acid the amounts of reactants which can be employed are such that the mol. ratio Ti:glycol or glycol ether is from 10:1 to 1:10, Ti:alkanolamine is from 6:1 to 1:4 and Ti:alphahydroxy acid is from 2:1 to 1:4. In the case of such a chelate when an inorganic base is reacted then usually the amount will be such that the mol. ratio of base to Ti is from 2:1 to 1:5. Where an organic base is used then the mol. ratio of base to Ti is from 2:1 to 1:5.

The paints of the present invention are aqueous emulsions of a binder which is a film-forming polymer. Such emulsions are also referred to as latex polymer dispersions which are obtained by emulsion polymerisation of one or more suitable monomers. Typical film-forming polymers include a wide range of homopolymers and copolymers of an ethylenically unsaturated monomer such as vinyl esters e.g. vinyl acetate and vinyl alcohol esters, alkyl acrylates and methacrylates e.g. methyl methacrylate, ethyl acrylate or ethyl hexyl acrylate, aliphatic and aromatic unsaturated hydrocarbon monomers such as ethylene butadiene or styrene and vinyl and vinylidene halides e.g. vinyl chloride and vinylidene chloride.

The aqueous emulsion paints can contain a suitable pigment or dye to improve the opacity and to colour the paint as is desired. Typical pigments which can be used are titanium dioxide pigments, zinc pigments, iron pigments, or magnesium pigments and, if desired an extender material such as a clay can also be incorporated.

Often the paint will also contain a thickener such as an acrylic copolymer or a compound based on cellulose such as carboxy methyl cellulose, hydroxy ethyl cellulose, hydroxy ethyl methyl cellulose etc.

Other conventional paint additives such as emulsifying agents, fungicides, biocides, antifoaming agents and anti-freezing agent can be present in the paint as is desired.

The paints of the present invention are prepared by mixing the desired ingredients under shear, usually in a high-speed mill until a homogeneous emulsion is obtained and the emulsion is then transferred to containers, e.g. those in which the paint is to be sold.

Typically the paint contains the described titanium chelate in an amount of from 0.10 to 5 per cent by weight based on the weight of the paint.

The invention is illustrated in the following Examples.

EXAMPLE 1

35.5 g of tetraisopropyl titanate, 53 g of diethylene glycol and 15.3 g of lactic acid were charged to a round-bottomed flask and mixed on a rotary evaporator with evolution of heat. 30.4 g of isopropyl alcohol were distilled off at 70° C. under reduced pressure. 5.4 g of triisopropanolamine, 2.9 g of monoethylene glycol and 13.4 g of a 95% solution of 2-amino, 2-methyl propan-1-ol in water were added in turn to the liquid in the rotary evaporator flask and thoroughly mixed to give a pale yellow liquid.

230 parts of rutile titanium dioxide, 97 parts of ground calcite, 25 parts of calcined china clay, 63 parts of a 3% aqueous solution of hydroxyethyl cellulose, 44 parts of a 5% aqueous solution of sodium hexametaphosphate, 12 parts of a 10% aqueous solution of a polyoxyalkene condensate, 1 part of a mercury fungicide, 171 parts of water and 11 parts of 2-butoxy ethyl acetate were mixed together and dispersed in a high speed mixer. To the resultant dispersion was added 335 parts of a vinyl acetate/2-ethyl hexyl acrylate copolymer emulsion and 1 part of 0.88 ammonia solution. To 100 g aliquots of the resultant paint was added 0.57 g of the above titanium chelate and the strength of the gel produced as a result of this addition was measured at intervals using a Boucher jelly tester. These gel strengths are compared with those achieved by using 0.5 g of a titanium chelate obtained from a titanium ortho ester, a glycol and an alkanolamine obtainable under the name TILCO AT33 per 100 g of paint in the following table.

TABLE

|  | 20 mins | 2 hours | 1 day | 1 week |
|---|---|---|---|---|
| TILCOM AT33 | 96 | 116 | 137 | 192 |
| EXAMPLE 1 | 63 | 86 | 135 | 200 |

EXAMPLE 2

71 g of tetraisopropyl titanate, 106 g of diethylene glycol and 27 g of lactic acid were mixed in a round-bottomed flask and 61 g of isopropyl alcohol were distilled off using the apparatus and conditions described in Example 1. 86.5 g of dibutylethanolamine were mixed in to give a yellow liquid. The product was added to paint made to the formulation described in Example 1 at 0.74 g per 100 g of paint and the gel strength produced compared with that produced with 0.5 g of the titanium and chelate described in Example 1 under the name TILCOM AT33 per 100 g of paint as shown in the following table.

TABLE

|  | 20 mins | 2 hours | 1 day | 2 weeks |
|---|---|---|---|---|
| TILCOM AT33 | 67 | 85 | 140 | 192 |
| EXAMPLE 2 | No gel | 70 | 150 | 229 |

EXAMPLE 3

71 g of tetraisopropyl titanate, 106 g of diethylene glycol and 27 g of lactic acid were mixed in a round-bottomed flask and 60 g of isopropyl alcohol were distilled off as in Example 1. 59.5 g of methyldiethanolamine were mixed in and the product was added to paint made to the formulation described in Example 1 at 0.66 g per 100 g of paint and the gel strength produced compared with that for 0.5 g of the titanium chelate described in Example 1 under the name TILCOM AT33 per 100 g of paint. The results are shown in the following table.

TABLE

|  | 20 mins | 2 hours | 1 day | 2 weeks |
|---|---|---|---|---|
| TILCOM AT33 | 67 | 85 | 140 | 192 |
| EXAMPLE 3 | No gel | 71 | 145 | 243 |

EXAMPLE 4

29.25 g of lactic acid, 11.9 g of potassium hydroxide, 106 g of diethylene glycol and 150 g of isopropyl alcohol were boiled under reflux in a round-bottomed flask fitted with stirrer, thermometer, dropping funnel and water-cooled condenser. 71 g of tetraisopropyl titanate were added slowly beneath the surface of the refluxing liquid to give a cloudy solution. The liquid was cooled to 60° C., transferred to a round-bottomed flask and isopropyl alcohol was distilled off under reduced pressure using a rotary evaporator. 12.53 g of triisopropanolamine were added and mixed in followed by 6.78 g of monoethylene glycol. The liquid was filtered to give a pale yellow hazy liquid. This product was used in paint made to the formulation described in Example 1 at 0.52 g per 100 g of paint and compared with 0.5 g of the titanium chelate described in Example 1 under the name TILCOM AT33 per 100 g of paint. The gel strengths produced are compared in the following table.

TABLE

|  | 20 mins | 2 hours | 5 days | 1 week |
|---|---|---|---|---|
| TILCOM AT33 | 87 | 107 | 161 | 160 |
| EXAMPLE 4 | 64 | 81 | 150 | 160 |

EXAMPLE 5

Using the apparatus described in Example 4, 31.5 g of lactic acid were added with stirring to 21.4 g of potassium carbonate and 150 g of isopropyl alcohol contained in the flask. The flask contents were boiled under reflux until reaction was complete (2 hours), giving a cloudy solution. 106 g of diethylene glycol were added in 5 minutes and the liquid heated to reflux during which time it became clear. 71 g of tetraisopropyl titanate were added beneath the surface of the boiling liquid in 30 minutes to give a hazy liquid. The liquid was boiled for a further 30 minutes, allowed to cool to 60° C. and transferred to a round-bottomed flask. Isopropyl alcohol was distilled off on a rotary evaporator under reduced pressure to give a cloudy liquid. 10.74 g of triisopropanolamine were added and mixed in followed by 5.81 g of monoethylene glycol. Filtration gave a clear pale yellow liquid.

The product was compared in paint made to the formulation described in Example 1 at 0.53 g per 100 g of paint with 0.5 g of the titanium chelate described in Example 1 under the name TILCOM AT33 per 100 g of paint. The gel strengths produced are compared in the following table.

TABLE

|  | 20 mins | 2 hours | 1 day | 1 week |
|---|---|---|---|---|
| TILCOM AT33 | 96 | 116 | 137 | 192 |
| EXAMPLE 5 | 63 | 85 | 136 | 193 |

EXAMPLE 6

Using the apparatus described in Example 4, 31.5 g of lactic acid, 150 g of isopropyl alcohol, 16.8 g of potassium hydroxide and 76 g of monopropylene glycol were heated to reflux and 71 g of tetraisopropyl titanate were added in 30 minutes beneath the surface of the liquid. The liquid was refluxed for a further 30 minutes, cooled to 60° C., transferred to a round-bottomed flask and isopropyl alcohol was distilled off under reduced pressure on a rotary evaporator. 10.74 g of triisopropanolamine were added to the slightly cloudy liquid and mixed in followed by 5.81 g of monoethylene glycol. Filtration gave a clear pale yellow liquid. The product was compared in paint made to the formulation described in Example 1 at 0.44 g per 100 g of paint with 0.5 g of the titanium chelate described in Example 1 under the name TILCOM AT33 per 100 g of paint. The gel strengths produced are compared in the following table.

TABLE

|  | 20 mins | 2 hours | 1 day | 1 week | 2 weeks |
|---|---|---|---|---|---|
| TILCOM AT33 | 61 | 78 | 161 | 184 | 213 |
| EXAMPLE 6 | No gel | 76 | 179 | 213 | 284 |

EXAMPLE 7

106 g of diethylene glycol, 71 g of tetraisopropyl titanate and 27 g of lactic acid were charged to a round-bottomed flask. The flask was transferred to a rotary evaporator and ammonia was bubbled into the liquid until pH 10 was achieved. 60 g of isopropyl alcohol were distilled off under reduced pressure at 70° C. 14.33 g of triisopropanolamine were added and mixed in followed by 7.75 g of monoethylene glycol to give a clear pale yellow liquid. The product was used in paint made to the formulation described in Example 1 to determine its shear resistance compared with the titanium chelate described in Example 1 under the name TILCOM AT33 using the following method.

To 300 g of paint which had been at 30° C. for 1 hour was added 0.9 g of the titanium chelate of this invention with stirring for 30 seconds using a spatula. The paint was then stirred for 1 hour in a water bath at 30° C. at a constant speed of 575 r.p.m. The paint was then divided into three aliquots and the gel strength of each sample measured at intervals as shown in the table below. To each of three 100 g aliquots of paint at 30° C. was added 0.3 g of this invention with spatula stirring for 30 seconds. The paint samples were kept at 30° C. for one hour and the gel strength measured at intervals. A similar series of tests were completed using 0.3 g of TILCOM AT33 per 100 g of paint. The "shear resistance" was determined from the gel strengths by expressing the sheared gel strength as a percentage of the unsheared gel strength. The results are shown in the table below.

TABLE

| Product | Test | 1 day | 1 week | 2 weeks |
|---|---|---|---|---|
| TILCOM AT33 | 1 hour shear | 92 | 138 | 145 |
|  | No shear | 110 | 156 | 167 |
|  | "Shear resistance" | 84% | 88% | 87% |
| Example 7 | 1 hour shear | 122 | 173 | 189 |
|  | No shear | 142 | 189 | 199 |
|  | "Shear resistance" | 86% | 92% | 95% |

EXAMPLE 8

71 g of tetraisopropyl titanate in 106 g of diethylene glycol were added to 14 g of potassium hydroxide, 31.5 g of lactic acid and 150 g of isopropyl alcohol at reflux temperature using the apparatus described in Example 4. Isopropyl alcohol was distilled off on a rotary evaporator at 70° C. under reduced pressure. 10.74 g of triisopropanolamine were added and mixed in followed by 5.81 g of monoethylene glycol to give a slightly hazy liquid.

880 g of water, 21 g of a 25% aqueous solution of a sodium carboxylate dispersing agent, 14 g of 2-amino, 2-methyl propan-1-ol, 1.4 g of fungicide, 52.5 g of 2-butoxy ethyl acetate and 10.5 g of an anti-foam agent were mixed and then 805 g of a rutile titanium dioxide 315 g of china clay and 185.5 g of whiting were added and dispersed using a high speed mill. A solution of 35 g of acrylic thickener in 186.1 g of water was added with stirring followed by 924 g of an ethylene/vinyl chloride/vinyl acetate terpolymer emulsion.

1.04 g of the titanium chelate of this invention per 100 g of paint made as above was compared with 1 g of the titanium chelate described in Example 1 under the name TILCOM AT33 per 100 g of paint using the test method described in Example 7. The gel strengths are shown in the following table.

TABLE

| Product | Test | 1 day | 1 week | 2 weeks |
|---|---|---|---|---|
| TILCOM AT33 | 1 hour shear | 120 | 138 | 149 |
|  | No shear | 189 | 208 | 200 |
|  | "Shear resistance" | 63% | 66% | 75% |
| Example 8 | 1 hour shear | 147 | 177 | 213 |
|  | No shear | 196 | 233 | 261 |
|  | "Shear resistance" | 75% | 76% | 82% |

EXAMPLE 9

71 g of tetraisopropyl titanate in 106 g of diethylene glycol were added to 17.5 g of potassium hydroxide, 31.5 g of lactic acid and 150 g of isopropyl alcohol at reflux temperature using the apparatus described in Example 4. Isopropyl alcohol was distilled off on a rotary evaporator at 70° C. under reduced pressure. 10.74 g of triisopropanolamine were added and mixed in followed by 5.81 g of monoethylene glycol to give a slightly hazy liquid.

1.06 g of this product was compared with 1 g of the titanium chelate described in Example 1 under the name TILCOM AT33 per 100 g of paint made to the formulation described in Example 8 using the test method described in Example 7. The gel strengths are shown in the following table.

TABLE

| Product | Test | 2 hours | 3 hours | 1 day | 1 week | 2 weeks |
|---|---|---|---|---|---|---|
| TILCOM AT33 | 1 hour shear | Not tested | Not tested | 142 | 154 | 162 |
|  | No shear | 156 | 159 | 179 | 191 | 199 |
|  | "Shear resistance" | — | — | 79% | 81% | 81% |
| Example 9 | 1 hour shear | Not tested | Not tested | 145 | 191 | 219 |
|  | No shear | 136 | 145 | 186 | 242 | 235 |
|  | "Shear resistance" | — | — | 78% | 79% | 93% |

We claimed:

1. An emulsion paint which comprises an aqueous dispersion of a film-forming polymer and a titanium chelate comprising the reaction product of a titanium orthoester, a glycol or glycol ether, an alkanolamine and an alpha-hydroxy carboxylic acid.

2. An emulsion paint according to claim 1 in which the titanium orthoester has the general formula Ti(OR)$_4$ in which R represents an alkyl group containing from 2 to 10 carbon atoms.

3. An emulsion paint according to claim 2 in which the titanium chelate has the general formula (Ti(OR)$_4$ in which R represents an alkyl group containing 2 to 4 carbon atoms.

4. An emulsion paint according to claim 1 in which the glycol is an alkylene glycol containing up to 6 carbon atoms.

5. An emulsion paint according to claim 1 in which the glycol ether is a monoalkyl ether of an alkylene glycol containing up to 6 carbon atoms in the alkylene group and in which the alkyl group contains up to 4 carbon atoms.

6. An emulsion paint according to claim 1 in which the alkanolamine is a monoalkanolamine, a dialkanolamine or a trialkanolamine.

7. An emulsion paint according to claim 1 in which the alpha-hydroxy carboxylic acid is an alpha-hydroxy mono carboxylic acid.

8. An emulsion paint according to claim 1 in which the alpha-hydroxy carboxylic acid is an alpha-hydroxy dicarboxylic acid.

9. An emulsion paint according to claim 1 in which the reaction product is also of a base.

10. An emulsion paint according to claim 1 in which the reaction product is also of a base selected from the class consisting of alkali metal hydroxides, alkali metal carbonates, alkali metal bicarbonates, ammonia and ammonia hydroxide.

11. An emulsion paint according to claim 1 in which in the titanium chelate the mol ratio Ti:glycol or glycol ether is from 10:1 to 1:10, the mole ratio Ti:alpha hydroxy carboxylic acid is from 2:1 to 1:4 and the mol ratio Ti:alkanolamine is from 6:1 to 1:4.

12. An emulsion paint according to claim 1 in which the reaction product is also of a base in the mol ratio Ti:base of from 2:1 to 1:5.

13. An emulsion paint according to claim 1 in which the filmforming polymer is a homopolymer or copolymer of an ethylenically unsaturated monomer.

14. An aqueous emulsion paint according to claim 1 in which the film-forming polymer is a polymer or copolymer of vinyl acetate.

15. An emulsion paint according to claim 1 in which there is present in the paint a pigment and/or dye.

16. An emulsion paint according to claim 1 in which the paint also contains a thickener.

17. An emulsion paint according to claim 1 in which the amount of the titanium chelate is from 0.1% to 5% by weight based on the weight of the paint.

* * * * *